United States Patent
Ichioka et al.

(10) Patent No.: US 8,568,323 B2
(45) Date of Patent: Oct. 29, 2013

(54) ULTRASOUND DIAGNOSIS APPARATUS AND A CENTESIS SUPPORTING METHOD

(75) Inventors: Kenichi Ichioka, Tochigi-ken (JP); Atsushi Sumi, Tochigi-ken (JP); Akihiro Kakee, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 399 days.

(21) Appl. No.: 12/729,971

(22) Filed: Mar. 23, 2010

(65) Prior Publication Data
US 2010/0240997 A1  Sep. 23, 2010

(30) Foreign Application Priority Data
Mar. 23, 2009  (JP) ................. P2009-070793

(51) Int. Cl.
*A61B 8/00*  (2006.01)
(52) U.S. Cl.
USPC ........................................... 600/443; 60/461
(58) Field of Classification Search
USPC .......... 600/407, 437, 464, 471, 443, 459, 461
See application file for complete search history.

(56) References Cited

U.S. PATENT DOCUMENTS

| 2007/0239004 A1* | 10/2007 | Kakee et al. .............. 600/437 |
| 2009/0198094 A1* | 8/2009 | Fenster et al. .............. 600/437 |
| 2010/0121189 A1* | 5/2010 | Ma et al. ..................... 600/437 |

OTHER PUBLICATIONS

Office Action mailed Jun. 14, 2013, in Japanese Patent Application No. 2009-070793, filed Mar. 23, 2009 (with English translation).

\* cited by examiner

*Primary Examiner* — Tse Chen
*Assistant Examiner* — Rochelle Reardon
(74) *Attorney, Agent, or Firm* — Oblon, Spivak, McClelland, Maier & Neustadt, L.L.P.

(57) ABSTRACT

An ultrasound diagnosis system and a centesis support controlling method by which positions and directions of a centesis needle traveling to a target region can accurately and easily be determined, including an MPR image data generating unit which generates target image data by setting a prescribed target MPR plane on volume data acquired through 3D scan over a 3D volume including a target region; a centesis needle MPR plane setting unit which generates centesis needle data indicating position and directions of the centesis needle, based on the acquired volume data; a crossing angle detection unit which detects a crossing angle between the target MPR plane and the centesis needle MPR plane including the centesis needle data; and a needling support data generating unit which generates needling support data by composing the target image data and the centesis needle data overlapped with centesis needle image data based on the detected crossing angle.

11 Claims, 13 Drawing Sheets

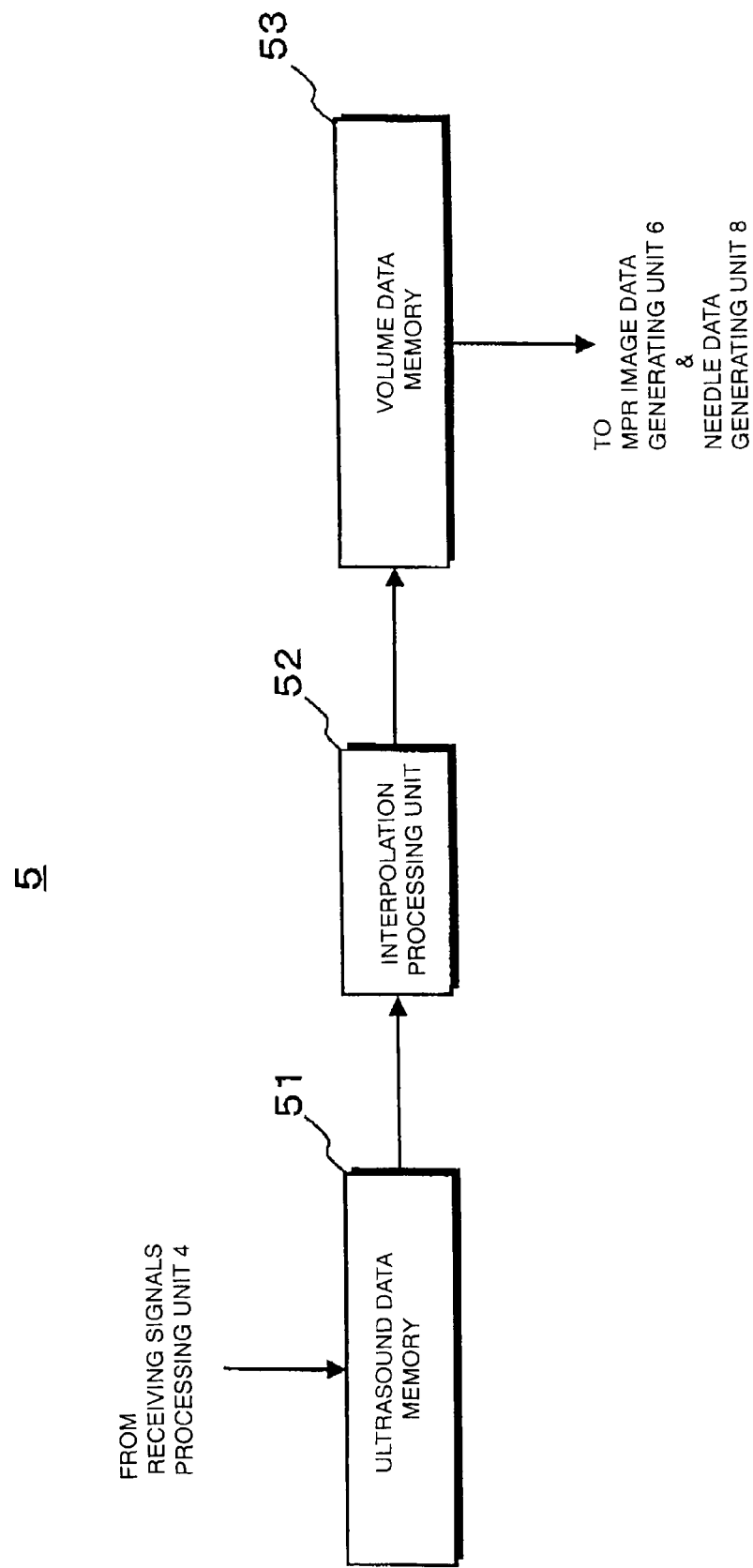

ULTRASOUND DIAGNOSIS APPARATUS AND A CENTESIS SUPPORTING METHOD

This application claims priority under 35 U.S.C. §119(a) from, and the benefit of, Japanese Patent Application No. 2009-70793 filed Mar. 23, 2009, the contents of which are expressly incorporated herein by reference in their entirety.

BACKGROUND OF THE INVENTION

A. Field of the Invention

The present invention relates to an ultrasound diagnosis apparatus and a centesis supporting method, and more particularly, to an ultrasound diagnosis apparatus and a centesis supporting method that can visually recognize a centesis needle insertion status into a target region in a patient by automatically tracking the inserted needle while observing ultrasound image data.

B. Background of the Invention

An ultrasound diagnosis apparatus transmits and receives ultrasound through a plurality of ultrasound transducers installed in a tip portion of an ultrasound probe to and from a diagnostic target region in an object. By simply touching an ultrasound probe to the surface of a patient's body, image data of the target region is generated. The generated image data can be displayed on a monitor in real time. An ultrasound diagnosis apparatus is widely used as an apparatus for diagnosing the status of various target organs in a patient's body.

Various conventional centesis supporting methods using an ultrasound diagnosis apparatus have been proposed for performing an invasive examination or medical treatment by means of a centesis needle (hereinafter, simply referred to as "needle") under observation of ultrasound image data (hereinafter, simply referred to as "image data") displayed in real time. By performing such centesis needle insertion into an examination/medical treatment target region (hereinafter, simply referred to as "target region") under observation of two dimensional (2D) image data or three dimensional (3D) image data of the ultrasound diagnosis apparatus, the proposed methods have improved safety and efficiency of the examination or medical treatment.

For instance, Japanese Patent Application Publication H6(1994)-205776 has proposed a centesis supporting method for performing a centesis into a target region under observation of ultrasound image data by mounting a centesis needle on a needling adapter attached to an ultrasound probe in order too generate and simultaneously display 2D image data of a centesis needle inserted into a patient body and a target region. By observing the 2D image data, a needle is inserted into the target region while confirming a position of the needle and an inserting direction.

Further, Japanese Patent Application Publication 2005-323669 has proposed another centesis supporting method for displaying data by composing a first image data including a target region generated based on volume data acquired from a 3D area in a patient and a second image data including a predetermined insertion pathway of a needle detected by a position sensor in a needling adapter.

According to these conventionally proposed centesis supporting methods, while the needle is accurately inserted along a preliminarily set up pathway (a predetermined inserting pathway, it is possible to travel a tip portion of the needle to the target region. However, in reality it actually happens that the needle is inserted in an unexpected direction due to unevenness of living body hardness along the predetermined inserting pathway. When the needle during travel slips off the predetermined inserting pathway, according to the conventional position detecting method using 2D image data, the needle disappears from the image data. Further, according to the conventional position detecting method using 3D image data, it also becomes impossible to accurately determines the position or the direction of the needle inserted into a body, since the needle is inserted in a different direction from the predetermined inserting pathway indicated on the image data detected by a position sensor.

SUMMARY OF THE INVENTION

The present invention addresses the above-mentioned and other problems and drawbacks, in order to provide a novel ultrasound diagnosis apparatus and a centesis supporting method that can accurately and easily determine a relative misalignment of a centesis needle to a target region, while the centesis needle inserted into a patient's body travels in an unexpected direction due to unevenness of anatomy hardness.

One aspect of the ultrasound diagnosis system consistent with the present invention is an ultrasound diagnosis apparatus configured to generate centesis support data based on volume data acquired from a 3D volume including a target region during a centesis needle insertion time, the ultrasound diagnosis apparatus comprising:

a centesis needle data generating unit configured to generate centesis needle data indicating a position and a direction of a centesis needle inserted in the 3D volume by processing the volume data;

a centesis needle MPR cross-sectional plane setting unit configured to set up a centesis needle MPR cross-sectional plane including the centesis needle data onto the volume data;

a crossing angle detecting unit configured to detect a crossing angle between a target MPR cross-sectional plane traversing the target region and set up on the volume data and the centesis needle MPR cross-sectional plane;

an MPR image data generating unit configured to generate a target image data on the target MPR cross-sectional plane of the volume data and a centesis needle image data on the centesis needle MPR cross-sectional plane;

a centesis support data generating unit configured to generate the centesis support data by composing the target image data and the centesis needle image data based on the crossing angle; and a display unit configured to display the centesis support data.

Another aspect of the ultrasound diagnosis system consistent with the present invention is an ultrasound diagnosis apparatus configured to generate centesis support data based on volume data acquired from a 3D volume including a target region during a centesis needle insertion time, the ultrasound diagnosis apparatus comprising:

an MPR image data generating unit configured to generate target image data on a target MPR cross-sectional plane traversing the target region set up to the volume data;

a centesis needle data generating unit configured to generate centesis needle data indicating a position or a direction of a centesis needle inserted into the 3D volume by processing the volume data;

a projection data generating unit configured to generate centesis needle projection data by projecting the centesis needle data on the target MPR cross-sectional plane;

a centesis support data generating unit configured to generate the centesis support data by overlapping the target image data with the centesis needle projection data; and a display unit configured to display the centesis support data.

One aspect of the centesis supporting method consistent with the present invention is a centesis supporting method used for an ultrasound diagnosis apparatus, the centesis support controlling method comprising:

processing volume data acquired from a 3D volume including a target region during a centesis needle insertion time;

generating centesis needle data for indicating a position or a direction of a centesis needle inserted into the 3D volume;

setting up a centesis needle MPR cross-sectional plane including the centesis needle data on the volume data;

detecting a crossing angle between a target MPR cross-sectional plane traversing the target region and set on the volume data and the centesis needle MPR cross-sectional plane;

generating target image data at the target MPR cross-sectional plane of the volume data and centesis needle image data at the centesis needle MPR cross-sectional plane;

generating the centesis support data by composing the target image data and the centesis needle image data based on the crossing angle; and displaying the centesis support data.

Another aspect of the centesis supporting method consistent with the present invention is a centesis supporting method used for an ultrasound diagnosis apparatus, the centesis support controlling method comprising:

generating target image data at a target MPR cross-sectional plane including a target region set to volume data acquired from a 3D volume including the target region during a centesis needle insertion time;

generating centesis needle data for indicating a position or a direction of a centesis needle inserted into the 3D volume by processing the volume data;

generating centesis needle projection data by projecting the centesis needle data on the target MPR cross-sectional plane;

generating the centesis support data by overlapping the centesis needle projection data onto the target image data; and displaying the centesis support data.

According to the present invention, it becomes possible to display a cross-sectional plane including a target set up by an operator and a scheduled pathway of a centesis needle overlapped with a centesis needle tracking plane generated by automatically detecting the centesis needle or overlapped with a projected image of the centesis needle. Consequently, it becomes possible to safely and efficiently perform an examination or medical treatments, even when a centesis needle inserted into a patient body travels in an unexpected direction, since it becomes possible to visually accurately and easily determine a relative misalignment of the centesis needle to a target region.

BRIEF DESCRIPTION OF THE DRAWINGS

The accompanying drawings, which are incorporated in and constitute part of this specification, illustrate various embodiments and/or features of the present invention, and together with the description, serve to explain embodiments of the present invention. Where possible, the same reference number will be used throughout the drawings to describe the same or like parts. In the drawings:

FIG. 4 is a block diagram illustrating the volume data generating unit in the ultrasound diagnosis apparatus shown in FIG. 1.

DESCRIPTION OF THE EMBODIMENTS

An ultrasound diagnosis apparatus consistent with the present invention firstly sets up a first multi-planar-reconstruction (MPR) cross-sectional plane (hereinafter, simply referred to as a first "MPR plane") including the target region. The first MPR plane is referred to as a target MPR plane. Further, the ultrasound diagnosis apparatus generates a target image data at the target MPR plane of volume data acquired through a 3D scan during the needle insertion time, and also generates centesis needle data indicating positions and directions of the needle based on the volume data. Then, the ultrasound diagnosis apparatus detects a crossing angle between a second MPR plane including the needle data (i.e., a centesis needle MPR plane) and the target MPR plane, and generates a second MPR image data (needle image data) by setting up the needle MPR plane on the volume data during the needle insertion time. The centesis support data is generated by composing the target image data and the needle image data overlapped with the needle data based on the crossing angle, In the following embodiments, the target image data and the centesis needle image data are generated by using the volume data acquired through a 2D array ultrasound probe. Of course, the volume data can be generated by mechanically moving 1D array ultrasound probes. It is further possible to generate the volume data based on another ultrasound data, such as color Doppler data.

Figure 1:
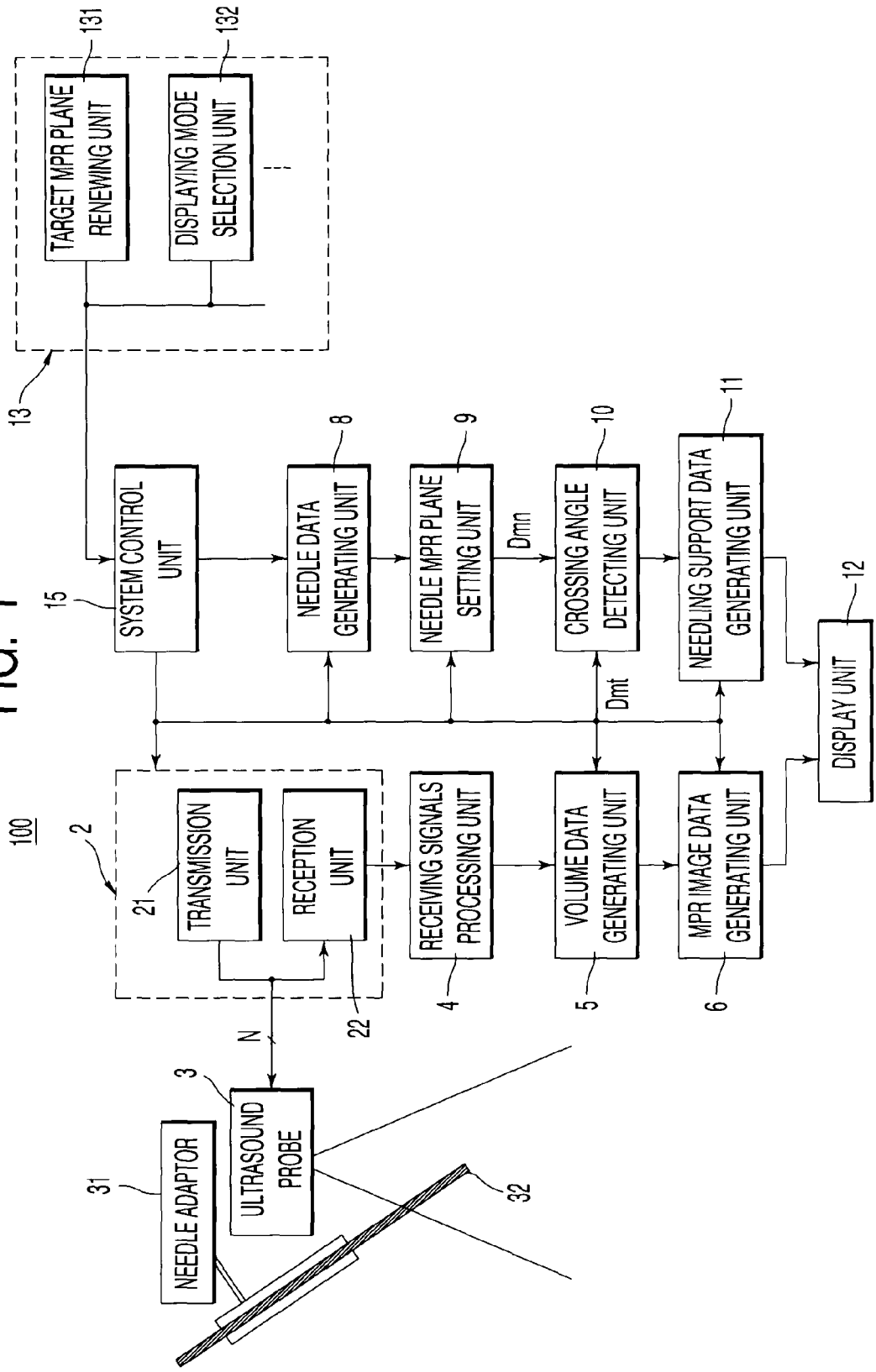
FIG. 1 is a block diagram illustrating an embodiment of the ultrasound diagnosis apparatus consistent with the present invention.

FIG. 1 is a block diagram illustrating an embodiment of an ultrasound diagnosis system 100 consistent with the present invention. The ultrasound diagnosis system 100 includes a transmission/reception unit 2, a 2-D ultrasound probe 3, a receiving signal processing unit 4, a volume data generating unit 5 and an MPR image data generating unit 6. The transmission/reception unit 2 supplies driving signals to a plurality of selected transducers in the ultrasound probe 3 for transmitting ultrasound pulses onto an object along prescribed directions. Further, the transmission/reception unit 2 performs phase compensation and summation of the plurality channel of receiving signals acquired through the selected transducers.

Thus, the 2-D ultrasound probe 3 transmits ultrasound pulses (transmission ultrasound) over a diagnosis target region in an object and converts ultrasound echo signals into electric signals (receiving signals). The receiving signal processing unit 4 generates ultrasound data (B mode data) by processing the receiving signals after arranging in phases and adding. The volume data generating unit 5 generates volume data by arranging the B mode data acquired through 3D scan on an object so as to correspond with the transmission and reception directions of ultrasounds. The MPR image data generating unit 6 generates a target image data and a needle image data by extracting each voxel of the volume data corresponding to the MPR planes set up by an input unit 13 or a needle MPR plane setting unit 9.

The ultrasound diagnosis apparatus 100 further includes a needle data generating unit 8, a needle MPR plane setting unit 9, a crossing angle detecting unit 10, a centesis support data generating unit 11, a display unit 12, an input unit 13 and a system control unit 15. The needle data generating unit 8 generates needle data indicating positions or directions of the needle by processing the volume data acquired during the needle insertion time. The needle MPR plane setting unit 9 sets up a needle MPR plane including the needle data. The crossing angle detecting unit 10 detects a crossing angle between a target MPR plane including a target region set up or renewed by the input unit 13 and the needle MPR plane.

The centesis support data generating unit 11 generates centesis support data by combining the target image data and the needle image data based on a detection result of the crossing angle. The input unit 12 displays the target image data generated by the MPR image data generating unit 6 before inserting the needle and the centesis support data generated by the centesis support data generating unit 11 during the needle insertion time. The input unit 13 inputs patient data and various command signals, and also performs various input operations, such as setting up acquiring conditions of volume data, renewing the target MPR plane, and selecting a displaying mode. The system control unit 15 totally controls each unit in the ultrasound diagnosis apparatus 100.

The ultrasound probe 3 includes a plurality (M) of 2D arrayed transducers (not shown) in a tip portion of the probe for transmitting ultrasound pulses over a 3D volume of a diagnosis object portion in an object. Ultrasound transmission and reception are performed by touching the tip portion of the probe to a body surface of a patient. Thus, the plurality (M) of transducers is coupled the transmission/reception unit 2 through a plurality (M) elements of a multi-core cable (not shown). On a side surface of the ultrasound probe 3, a needling adapter 31 is mounted. The needling adapter 31 includes a needle guide (not shown) for inserting a centesis needle 32 into a patient body. By the needle guide of the needling adapter 31, a predetermined insertion pathway of the needle 32 to the volume data is automatically decided.

In this embodiment, 2D array sector scanning ultrasound probe 3 is used for scanning ultrasound. Of course, it is possible to use another type of ultrasound probe, such as a linear scanning type ultrasound probe or a convex scan type ultrasound probe.

Figure 2:
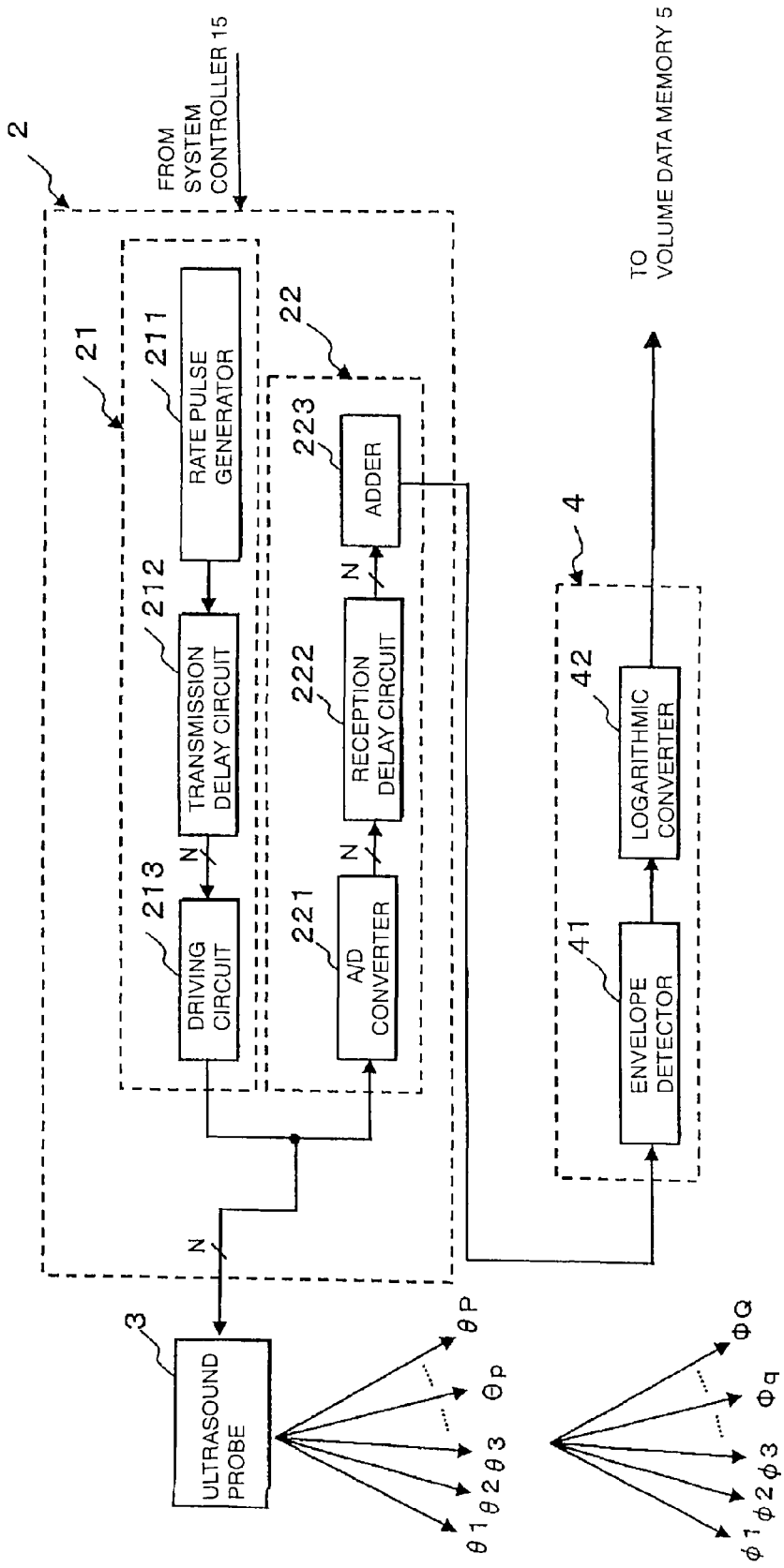
FIG. 2 is a block diagram illustrating the transmission and reception unit, and the receiving signal processing unit in the ultrasound diagnosis apparatus shown in FIG. 1.

As illustrated in FIG. 2, the transmission/reception unit 2 includes a transmission unit 21 for driving a plurality (Mt) of transmission signals to the selected plurality (Mt) of transmitting transducers in the ultrasound probe 3 and a reception unit 22 for converting a plurality (Mr) of ultrasound echo signals supplied from the selected plurality (Mr) of receiving transducers.

The transmission unit 21 includes a rate pulse generator 211, a transmission delay circuit 212 and a driving circuit 213. The rate pulse generator 211 generates rate pulses which determine a recycle period for transmission ultrasound by diving a reference signal supplied from the system control unit 15. The generated rate pulses are supplied to the transmission delay circuit 212. The transmission delay circuit 212 includes a plurality of independent delay circuits of the same number M of 2D array transducers as used for transmission in order to drive a selected number Mt among the plurality number (M) of transducers. The transmission delay circuit 212 gives a convergence delay time for converging the transmission ultrasound into a prescribed depth and a deviation delay time for transmitting ultrasound in a prescribed transmission/reception direction ($\theta p$, $\phi q$) to the rate pulses and supplies to the driving circuit 213. The plurality (N) of driving circuits 213 drive the selected number N of transducers for transmitting ultrasound based on the rate pulses.

The reception unit 22 includes a plurality (N) of A/D converters 221, a plurality (N) of reception delay circuits 222 for selected reception channels and a summation circuit 223. The plurality of receiving signals supplied from the transducers is converted into digital signals in the A/D converters 221

The reception delay circuit 222 gives each of the reception signals outputted from the A/D converter 221 a convergence delay time for converging reception ultrasound from a prescribed depth and a deviation delay time for setting reception directivity to a prescribed direction ($\theta p$, $\phi q$). The reception signals acquired from the prescribed direction are added in the summation circuit 223. The delay time of the reception delay circuit 222 is controlled by the scan control unit 12.

Figure 3B:
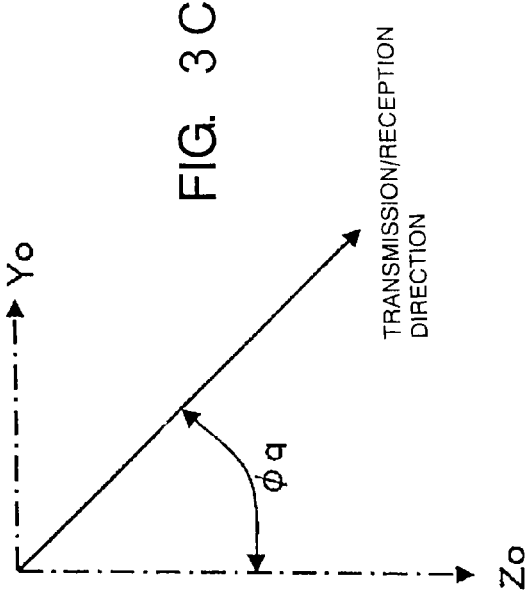
FIG. 3B illustrates the direction of ultrasound transmission and reception projected on the x-z plane in the volume scan shown in FIG. 3A.
Figure 3C:
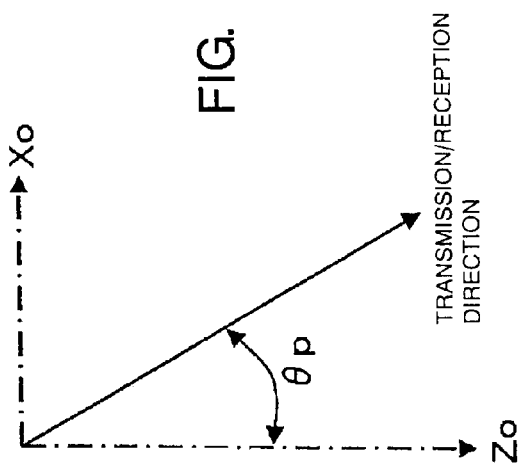
FIG. 3C illustrates the direction of ultrasound transmission and reception projected on the y-z plane in the volume scan shown in FIG. 3A.
Figure 3A:
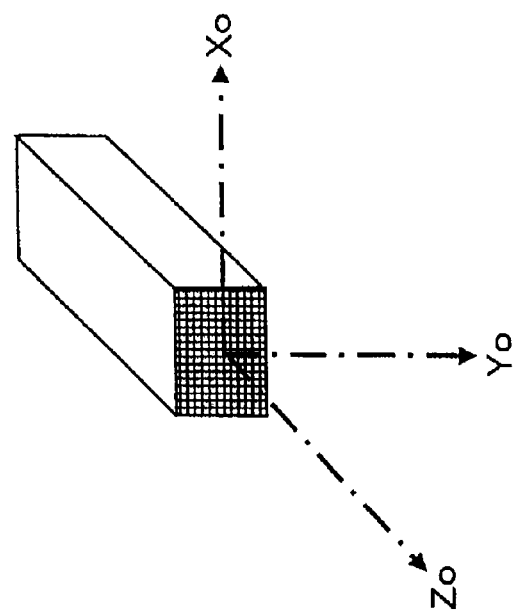
FIG. 3A illustrates the direction of ultrasound transmission and reception in a 3D (volume) scan by 2D array transducers provided in an ultrasound probe.

FIGS. 3A-3C illustrate ultrasound transmission/reception directions ($\theta p$, $\phi q$) at an orthogonal coordinate system [x, y, z] where a center axis of the ultrasound probe 3 is set as the z-axis. In FIGS. 3B and 3C, each angles $\theta p$ and $\phi q$ indicates an angle a projected transmission/reception direction to the z-axis on an x-z plane and a y-z plane, respectively.

As illustrated in FIG. 3A, the transducers 31 are two dimensionally arranged in both the x-axis (azimuth) direction and the y-axis (elevation) direction. In accordance with scan controlling signals supplied from the scan control, the delay time in the transmission delay circuit 212 in the transmission unit 21 and the reception delay circuit 222 in the reception unit 22 is controlled in order to perform a volume scan on a 3D region including a diagnosing target region of an object.

As illustrated in FIG. 2, the reception signals processing unit 4 includes an envelope detector 41 and a logarithmic converter 42. The envelope detector 41 detects the envelope of the reception signals supplied from the summation circuit 223 in the reception unit 22. The logarithmic converter 42 generates B mode data by converting the amplitude of the envelope detected reception signals. It is possible to replace of the positions of the envelope detector 41 and the logarithmic converter 42.

As illustrated in FIG. 4, the volume data generating unit 5 includes an ultrasound data memory unit 51, an interpolation processing unit 52 and a volume data memory unit 53. However, it is possible to eliminate the interpolation processing unit 52. The ultrasound data memory unit 51 stores a plurality of ultrasound data generated in the reception signals processing unit 4 based on reception signals collected by a 3D scan on each of the plurality of 3D regions that are set on a diagnosis object portion in an object with accompanying of ultrasound transmission/reception direction data.

The interpolation processing unit forms 3D ultrasound data by arranging the plurality of B mode data that are read out from the B mode data memory unit in accordance with the transmission/reception directions at a prescribed time phase. The interpolation processing unit 52 further generates volume data that is constructed with equidistant distance voxels by interpolating unequal distance voxels for constructing the 3D ultrasound data. As explained above, it is possible to directly generate the volume data without performing interpolations. The acquired volume data are stored in the volume data memory unit 53.

Before a centesis needle is inserted into a patient, the MPR image data generating unit 6 shown in FIG. 1 reads out the volume data from the volume data memory unit 53 in the volume data generating unit 5. Further, the MPR image data generating unit 6 generates target image data by extracting a voxel of the volume data corresponded to a preliminarily set up target MPR plane or a renewed target MPR plane by the input unit 13. Similarly, when the centesis needle has been inserted in the patient, the MPR image data generating unit 6 reads out the volume data stored in the volume data memory unit 53, and generates both of target image data and centesis needle image data by extracting voxels of the volume data corresponded to the target MPR plane and to a centesis needle MPR plane set up by the needle MPR plane setting up unit 9.

The target MPR plane is initially set up, for instance, at the Xo-Zo plane as shown in FIG. 3B. If it is judged that the position of the target MPR plane is inadequate by observing the target image data acquired at this time, the position of the target MPR plane is revised to an adequate position by using the target MPR plane revising unit 131 in the input unit 13.

Figure 5B:
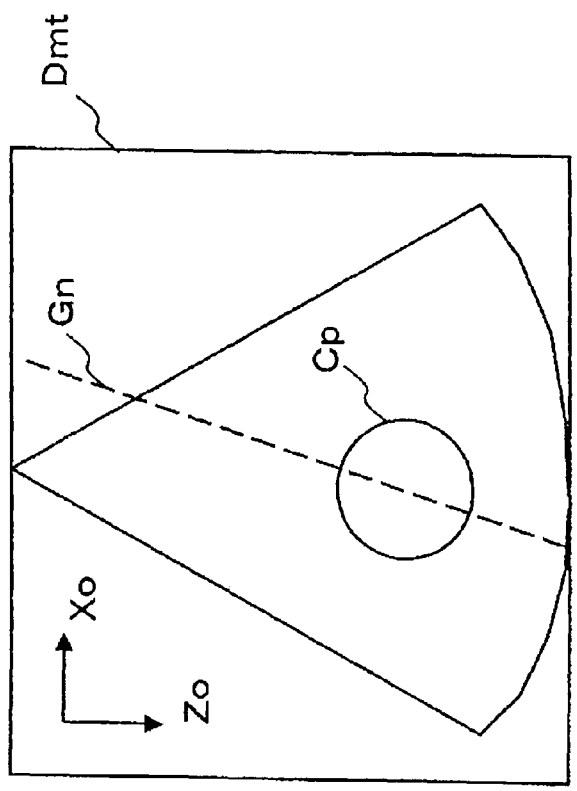
FIG. 5B illustrates target image data generated on the target MPR cross-sectional plane shown in FIG. 5A.
Figure 5A:
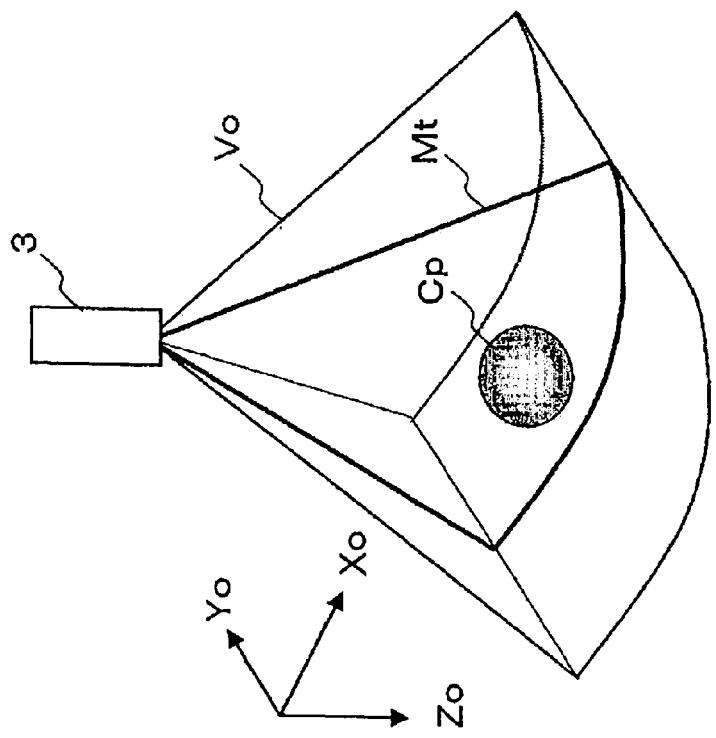
FIG. 5A illustrates a target MPR cross-sectional plane Mt set on a volume data.

FIG. 5A illustrates the volume data Vo acquired from a 3D area including a target region Cp. Initially, a target MPR plane Mt is set up at the Xo-Zo plane (FIG. 3B) in this 3D area. FIG. 5B illustrates an example of the target image data Dmt generated at the target MPR plane Mt and displayed on the display unit 12. An insertion marker Gn for indicating an expected insertion pathway of the centesis needle 32 is automatically set up in a surface of the target MPR plane Mt and displayed on a monitor in the display unit 12 overlapped on the target image data Dmt. By observing the target image data Dmt displayed time sequentially, an operator adjusts a position and a direction of the ultrasound probe 3 on a body surface of a patient so that the insertion marker Gn of the centesis needle 32 crosses with the target region Cp.

The needle data generating unit 8 (FIG. 1) includes a comparison circuit (not shown) for comparing the voxel value of the volume data supplied from the volume data generating unit 5 at the needle insertion time and a prescribed threshold value α for detecting voxel. Based on a result of the comparison, a linear needle data for indicating positions and directions of the centesis needle 32 is generated by extracting the reception ultrasound obtained from a surface of the centesis needle 32 and have relatively large amplitude.

The needle MPR plane setting unit 9 detects position data in the centesis needle data and sets up needle MPR plane including the centesis needle data to the volume data based on the detected position data. If the centesis needle data does not exist on the same plane, the needle MPR plane is set up, for instance, on a plane where a square sum of distances from each of voxels forming the centesis needle data becomes a minimum.

The crossing angle detection unit 10 detects a crossing angle β between the target MPR plane Mt and the needle MPR plane Mn based on a preliminarily set up target MPR plane or a position data of a renewed target MPR plane by the input unit 13 and the needle MPR plane position data set up by the needle MPR plane setting unit 9.

The centesis support data generating unit 11 receives target image data and centesis needle image data supplied from the MPR image data generating unit 6 during centesis needle insertion, and also receives crossing angle data β between the target MPR plane supplied from the crossing angle detection unit 10 and the needle MPR plane. Based on the crossing angle data β, the centesis support data generating unit 11 generates centesis support data by composing the target image data and the centesis needle image data. Based on the crossing angle β, it is also possible to compose the linear centesis needle data generated by the centesis needle data generating unit 8 by overlapping the centesis needle image data with the target image data. According to this method, it becomes much easier to figure out a relative position relationship of the centesis needle to the target region.

Referring to FIG. 1, the display unit 12 includes a display data generating unit, a data conversion unit and a monitor (all not shown). The display unit 12 displays the target image data generated by the MPR image data generating unit 6 before insertion of the needle and the centesis support data generated by the centesis support data generating unit 11 during the centesis needle insertion time on the monitor by performing prescribed display format conversions.

The display data generating unit in the display unit 12 generates display data by adding appendix data, such as patient data, to the target image data supplied from the MPR image data generating unit 6 and the centesis support data supplied from the centesis support data generating 11. The data conversion unit in the display unit 12 displays the display data generated in the display data generating unit on the monitor by performing conversion processes, such as digital-to-analog (D/A) conversion and television format conversion.

Figures 6A, 6B:
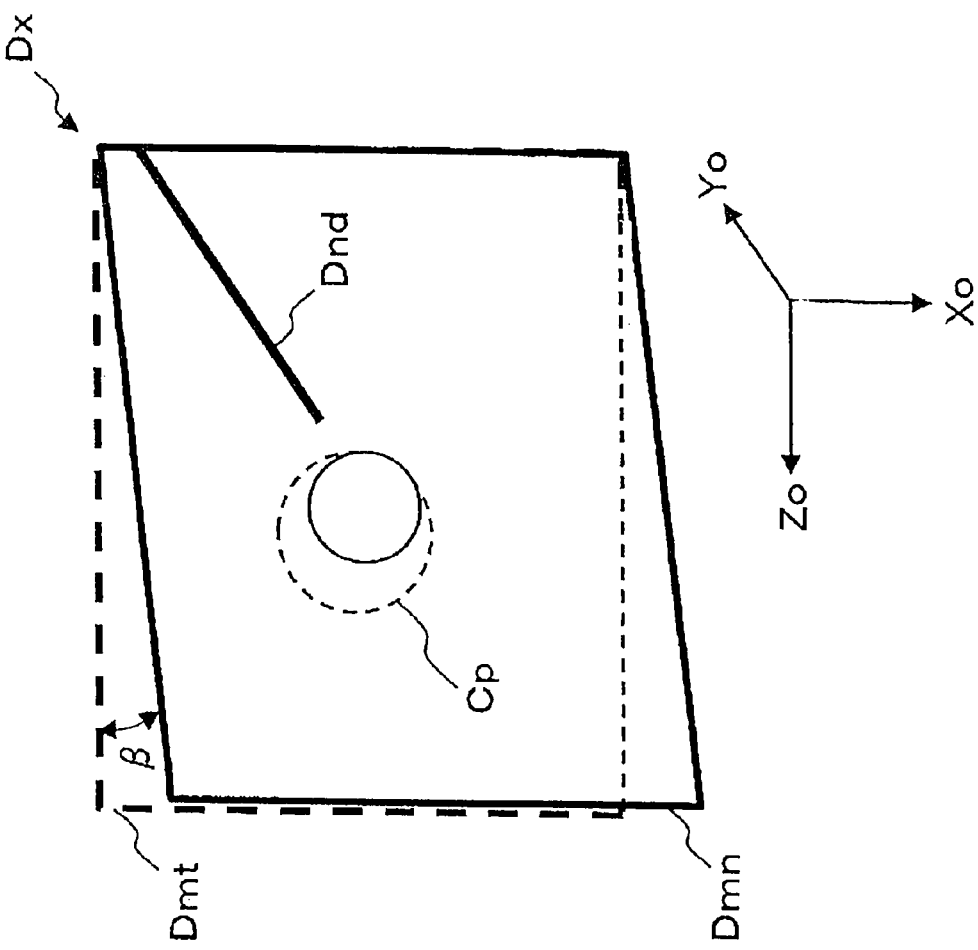
FIG. 6A illustrates a target MPR cross-sectional plane and a centesis needle MPR cross-sectional plane set to the target region during a centesis needle insertion time.
FIG. 6B illustrates an example display of the centesis support data on a monitor.

FIG. 6A shows a target MPR plane Mt and a centesis needle MPR plane Mn that are set up against the target region during a centesis needle insertion time into a patient body. As illustrated in FIG. 6A, the target MPR plane Mt is set up on the Xo-Zo plane that crosses with the target region Cp of the volume data acquired during the centesis needle insertion time. The centesis needle MPR plane Mn is set up so as to cross the target region Cp upon crossing the target MPR plane Mt at a crossing angle β based on the centesis needle data of the centesis needle 32 acquired by processing the volume data.

FIG. 6B is an example of the centesis support data displayed on a monitor in the display unit 12 at this time. As illustrated in FIG. 6B, the centesis support data Dx is acquired by composing the target image data Dmt generated on the target MPR plane Mt and the centesis needle image data Dmn generated on the centesis needle MPR plane Mn based on the crossing angle data β between these MPR planes. The acquired centesis support data Dx is displayed.

When the centesis support data Dx acquired by composing the target image data Dmt and the centesis needle image data Dmn is displayed, the display data generating unit in the display unit 12 sets up, for instance, a warm color tone having a transparency in accordance with the crossing angle to the centesis needle image data Dmn that locates at a front position against the position of the target image data Dmt. Further, the display data generating unit sets up a cold color tone having a transparency in accordance with the crossing angle to the centesis needle image data Dmn that locates at a backward position against the position of the target image data Dmt.

Generally, it is desirable to set up such a larger transparency as the larger crossing angle between the target MPR plane Mt and the centesis needle MPR plane Mn. However, it is not limited. Of course, it is possible to set up a cold color tone to the centesis needle image data Dmn locating at a front position of the target image data Dmt, and to set up a warm color tone to the centesis needle image data Dmn located at a backward position of the target image data Dmt.

Figure 7A:
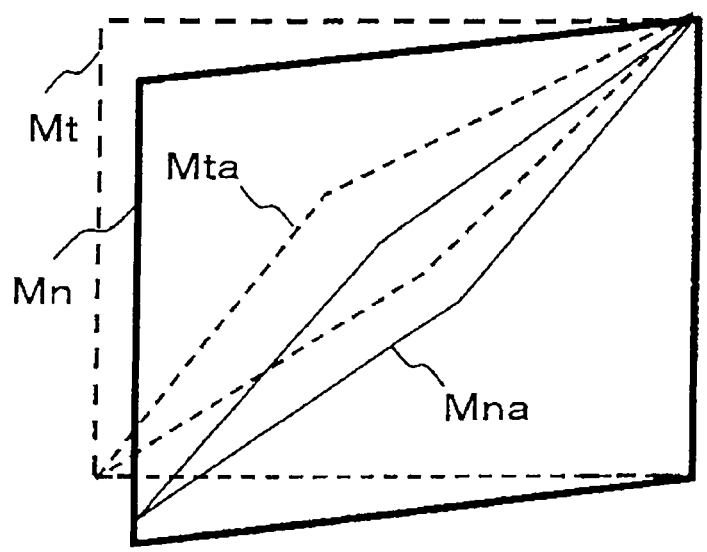
FIG. 7A illustrates a target MPR cross-sectional plane orthogonal to the target MPR cross-sectional plane shown in FIG. 6A, and a centesis needle MPR cross-sectional plane orthogonal to the centesis needle MPR cross-sectional plane shown in FIG. 6A.
Figure 7B:
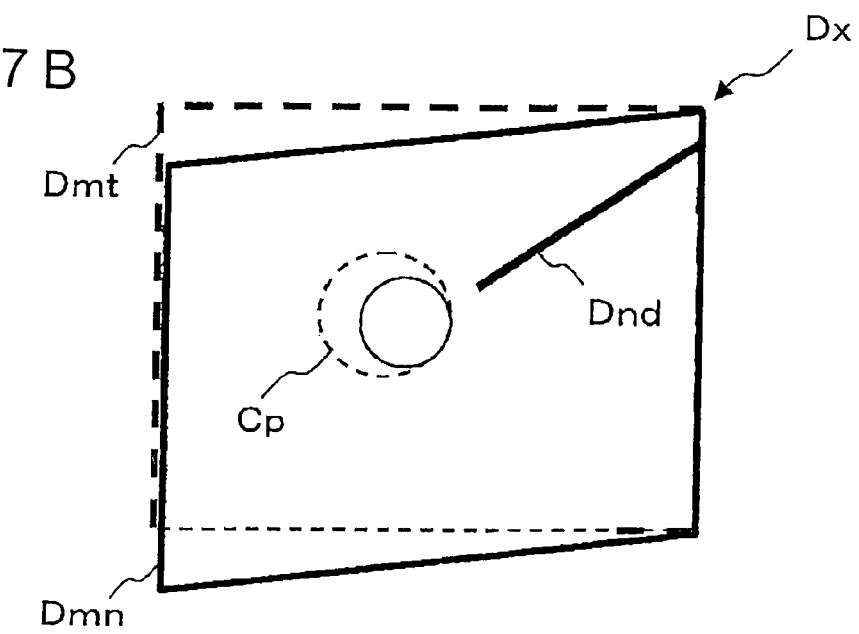
FIG. 7B illustrates a centesis support data generated and composed at a centesis needle MPR cross-sectional plane.
Figure 7C:
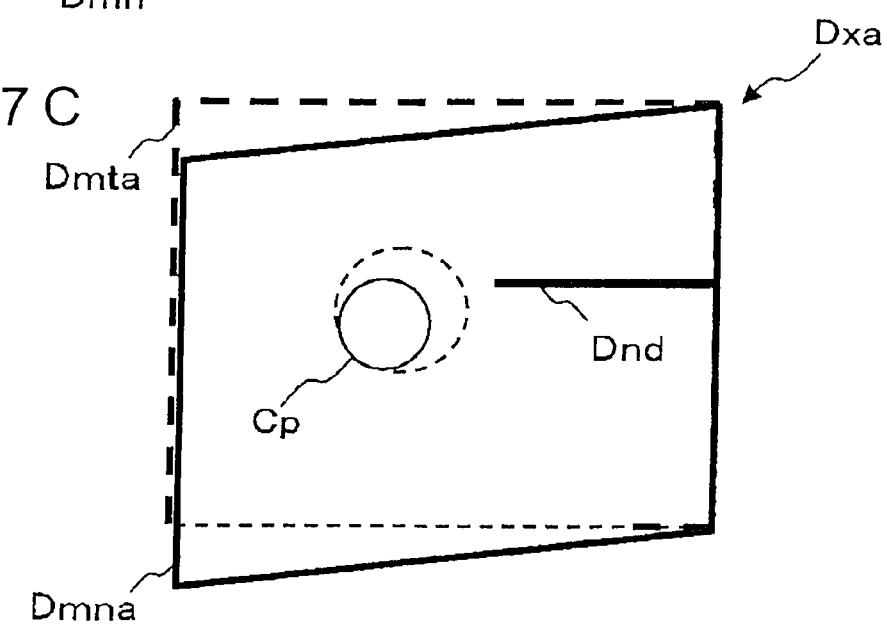
FIG. 7C illustrates a centesis support data generated and composed at another centesis needle MPR cross-sectional plane.

FIGS. 7A-7C illustrate another example of display of the centesis support data displayed on the display unit 12 during a needle insertion time into a patient body. As illustrated in FIG. 7A, in addition to the target MPR plane Mt and the centesis needle MPR plane Mn as shown in FIG. 6A, a target MPR plane Mta that is orthogonal to the target MPR plane Mt and a centesis needle MPR plane Mna that is orthogonal to the centesis needle MPR plane Mn are set up on the volume data acquired during the centesis needle insertion time.

As similar as shown in FIG. 6B, a centesis support data Dx is generated by composing the target image data Dmt generated on the target MPR plane Mt and the centesis needle image data Dmn generated on the centesis needle MPR plane M, and displayed on the display unit 12 (FIG. 7B). As illustrated in FIG. 7C, a centesis support data Dxa is displayed on the display unit 12 by composing the target image data Dmta generated on the target MPR plane Mta and a centesis needle image data Dmna generated on the centesis needle MPR plane Mna. In this case, a similar transparency and a similar color tone as in FIG. 6B is respectively set up to display the centesis needle image data Dmn and the centesis needle image data Dmna.

A display mode selection for the centesis support data that is acquired by composing one target image data and centesis needle image data as shown in FIG. 6B, and a display mode selection for the centesis support data that is acquired by composing a plurality of target image data and centesis needle image data as shown in FIGS. 7B and 7C are performed through a display mode selection unit 132 included in the input unit 13 shown in FIG. 1.

In FIG. 1, the input unit 13 includes input devices such as a display panel, a key board, a trackball and a mouse on a display panel. The input unit 13 includes a target MPR plane revising unit 131 for revising the target MPR cross-sectional plane and the display mode selection unit 132 for selecting the display mode. The input devices performs various input and set up operations, such as an input of patient data, a set up of volume data acquisition conditions, a set up of the threshold value α necessary for generating the centesis needle data and inputs of various command signals.

The system control unit 15 includes a central processing unit (CPU) and a memory circuit (both not shown). The memory circuit stores various data input, set up or selected through the input unit 13. The CPU in the system control unit 15 controls each unit in the ultrasound diagnosis apparatus 100 and also controls generation and display of the centesis support data against the target region based on the various input, set up and selected data.

Figure 8:
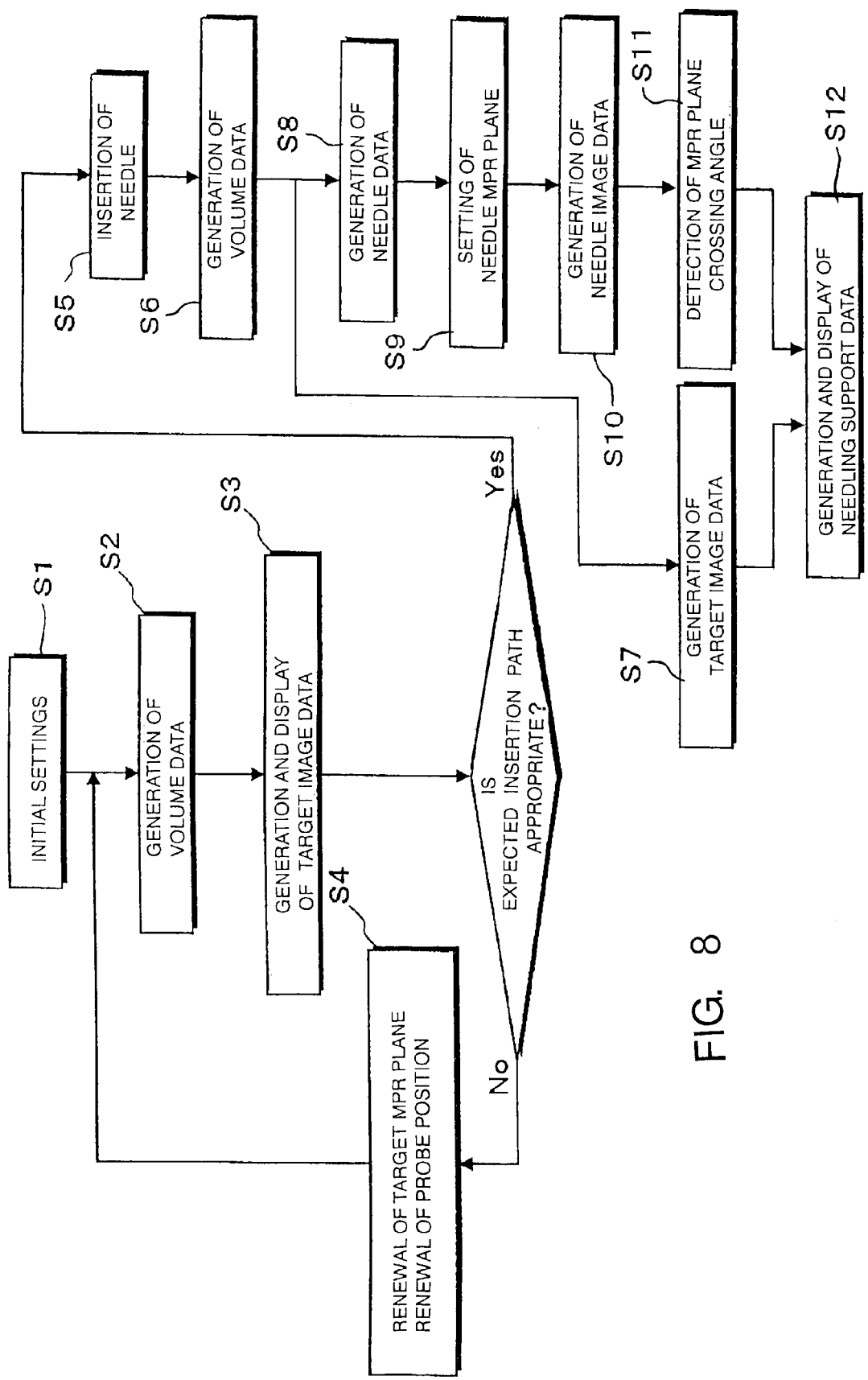
FIG. 8 is a flowchart illustrating steps for displaying the centesis support data.

FIG. 8 is a flowchart illustrating a process for displaying the centesis support data consistent with the present invention. Prior to start of acquisition of volume data of a 3D area including a target region, an operator of the ultrasound diagnosis apparatus 100 inputs patient data through the input unit 13, and further establishes initial settings of the apparatus, such as settings up of volume data acquisition conditions, a target MPR plane and a threshold value α for generating centesis needle data, and a selection of display mode (FIG. 8, step S1). In this embodiment, the input unit 13 sets up the Xo-Zo plane shown in FIG. 3 as the first target MPR cross-sectional plane. Further, the input unit 13 selects the centesis support data acquired by composing one target image data and the centesis needle image data as shown in FIG. 6B as a display mode. The inputted, selected and set up data through the input unit 13 are stored in the memory circuit in the system control unit 15.

After finishing the initial settings, the operator inputs a volume data acquisition start command through the input unit 13 with contacting a tip portion of the ultrasound probe to a patient body surface. By supplying the acquisition start command signal from the system control unit 15, an acquisition of volume data is started.

To acquire the volume data, the rate pulse generator 212 in the transmission unit 21 (FIG. 2) generates rate pulses in accordance with the control signals supplies from the system control unit 15. The generated rate pulses are supplied to the transmission delay circuit 212. The transmission delay circuit 212 in the transmission unit 21 gives a focusing delay time for focusing transmitted ultrasounds a prescribed depth and a deflection delay time for emitting the transmitted ultrasounds along the first transmission/reception direction ($\theta 1, \phi 1$) to the rate pulses. The rate pulses are supplied to a plurality (N) channels of driving circuits 213. The driving circuits 213 in the transmission unit 21 generate driving signals having a prescribed delay time based on the rate pulse supplied from the transmission delay circuit 212. The driving signals are supplied to a plurality (N) of transducers in the ultrasound probe 3 for emitting transmission ultrasounds to the first transmission/reception direction ($\theta 1, \phi 1$) of the patient body.

A portion of the emitted transmission ultrasounds are reflected at boundaries of the internal-organs having different acoustic impedances. The reflected ultrasounds are received and converted into a plurality (N) channel of receiving signals through the transducers in the ultrasound probe 3. After converting the receiving signals to digital signals at the analog to digital (A/D) converter 221 in the reception unit 22, a plurality (N) channel of reception delay circuits 222 give delay times for converging the receiving ultrasounds from a prescribed depth and setting up a strong receiving directivity to the receiving ultrasounds from the transmission/reception directions ($\theta 1, \phi 1$). The converged receiving ultrasounds are phase compensated and summed in the adder 223.

The phase compensated and summed receiving signals are supplied to the receiving signal processing unit 4. The receiving signal processing unit 4 includes an envelope detector 41 and a logarithmic converter 42 for generating B mode data by performing envelope detection and logarithmic conversion of the receiving signals. The generated B mode data is stored in the ultrasound data memory 51 of the volume data generating unit 5.

After finishing of generation and storing of B mode data along the transmission/reception directions ($\theta 1, \phi 1$), the following ultrasound transmission/reception is similarly performed along the transmission/reception direction ($\theta 1, \phi 2$ to $\phi Q$) that is set up by renewing the $\phi$ direction by $\Delta\phi$ and $\phi q=1+(q-1)\Delta\phi(q=2$ to Q). At this time, the system control unit 15 renews the delay times in the transmission delay circuit 212 and the reception delay circuit 222 in accordance with the ultrasound transmission/reception directions.

When the ultrasound transmission/receptions along the transmission/reception directions (θ1, φ1 to φQ) have finished, the transmission/receptions θp=θ1+(p−1)Δθ(p=2 to P) are set up by renewing the θ direction by Δθ. A 3D scan is performed by repeating these φ1 to φQ ultrasound transmissions/receptions in each of the transmission/reception directions θ2 to θP. The B mode data acquired through the ultrasound transmissions/receptions in each of the transmission/reception directions are stored in the ultrasound data memory 51 of the volume data generating unit 5. The interpolation processing unit 52 in the volume data generating unit 5 generates volume data based on the ultrasound data stored in the ultrasound data memory 51 and the generated volume data is stored in the volume data memory unit 53 (FIG. 8, step S2).

Next, the MPR image data generating unit 6 generates a target image data by extracting the voxel of the Xo-Zo plane that is initially set up as a first target MPR plane among the volume data stored in the volume data memory unit 53. The generated target image data is displayed on a monitor in the display unit 12 overlapped with the insertion marker indicating a planned inserting pathway of the centesis needle (FIG. 8, step S3).

By observing the target image data overlapped with the insertion marker on the display unit 12, an operator judges whether the position of the target MPR plane to the target region and the position of the predetermined insertion marker are appropriate or not. If the operator judges these positions are inappropriate, the operator revises the position of the target MPR plane by using the target MPR plane revising unit 131 in the input unit 13 while changing the position and direction of the ultrasound probe 3 on the patient body surface (FIG. 8, step S4).

After revising the position of the target MPR plane with changing the position and direction of the ultrasound probe 3, by returning to the step S2 in FIG. 8, the volume data generating unit 5 generates new volume data based on the receiving signals acquired at the changed position of the ultrasound probe 3. Further, at the step S3 in FIG. 8, the MPR image data generating unit 6 generates the target image data on the revised target MPR plane for display with the insertion marker on the display unit 12. Until the insertion marker is set up at an appropriate position of the target region, the steps S2 to S4 in FIG. 8 are repeated.

When the insertion marker is set up an appropriate position of the target region, the operator places a centesis needle 32 on a needle guide of a needling adapter 31 that is mounted on the tip portion of the ultrasound probe 3 and the centesis needle 32 is inserted to the target region in the patient body (FIG. 8, step S5).

Then, the start command for acquiring the volume data is again input through the input unit 13. According to the similar step of the step S2, the volume data generating unit 5 generates the volume data during the centesis needle insertion time (FIG. 8, step S6). The generated volume data is stored in the volume data memory unit 53.

The MPR image data generating unit 6 generates the target image data by extracting the voxel on the target MPR plane from among the volume data that are stored in the volume data memory unit 53 during the centesis needle insertion time (FIG. 8, step S7).

The centesis needle data generating unit 8 extracts the voxel corresponding to echo ultrasounds reflected from the surface of the centesis needle 32 by comparing the voxel value of the volume data acquired during the centesis needle insertion time with a prescribed threshold value α for detecting voxels. By processing these voxels, the centesis needle data generating unit 8 generates a linear centesis needle data indicating the position and direction of the centesis needle 32 (FIG. 8, step S8).

The centesis needle MPR plane setting unit 9 detects the position data of the centesis needle data supplied from the centesis needle data generating unit 8. Based on the detected position data, the centesis needle MPR plane setting unit 9 sets up the centesis needle MPR plane including the centesis needle data (FIG. 8, step S9).

The MPR image data generating unit 6 reads out the volume data stored in the volume data memory unit 53 of the volume data generating unit 5 during the centesis needle insertion time, and generates centesis needle image data by extracting the voxel of the volume data corresponded to the centesis needle MPR plane set up by the centesis needle MPR plane setting unit 9 (FIG. 8, step S10).

The crossing angle detection unit 10 detects a crossing angle between the target MPR plane and the centesis needle MPR plane based on the preliminary set up target MPR plane or the position data of the target MPR plane revised by the input unit 13 and the position data of the centesis needle MPR plane set up by the centesis needle MPR plane setting unit 9 (FIG. 8, step S11).

The centesis support data generating unit 11 receives the target image data and the centesis needle image data that are supplied from the MPR image data generating unit 6 during the centesis needle insertion time, the crossing angle data supplied from the crossing angle detection unit 10 and the centesis needle data supplied from the centesis needle data generating unit 8, and generates the centesis support data by composing the centesis needle image data overlapped with the centesis needle data and the target image data based on the crossing angle data. The generated centesis support data undergoes a prescribed conversion process in the display unit 12 for displaying on the monitor (FIG. 8, step S12).

By repeating the above-mentioned steps S5 to S12 or steps S2 to S12, the centesis support data are generated and displayed in time series. Under observation of the centesis support data, the centesis needle is inserted to the target region.

In the present embodiment, the centesis support data Dx is generated by composing the centesis needle image data Dmn overlapped with the centesis needle data Dnd and the target image data Dmt. It is also possible to compose the centesis needle image data Dmn that does not overlap with the centesis needle data Dnd and the target image data Dmt.

Further, in the present embodiment, a color tone and a transparency are set up to the centesis needle image data Dmn. Of course, it is possible to set up either one of the color tone or the transparency. Further, it is possible to set up the color tone or the transparency to the target image data Dmt.

According to the disclosed embodiment, while the centesis needle inserted into the patient body travels in an unexpected direction, it becomes possible to accurately and easily determine a relative positioned relationship of the centesis needle to the target region. Consequently, it becomes possible to safely perform an examination or a medical treatment with high efficiency.

In the present embodiment, the target MPR plane including the target region and the centesis needle MPR plane including the centesis needle are independently set up, and the centesis support data is generated by composing target image data on the target MPR plane and the centesis needle image data on the centesis needle MPR plane based on the crossing angle data between the target MPR plane and the centesis needle MPR plane. Consequently, a misalignment of the centesis needle to the target region can easily be determined. Further, it becomes possible to accurately observe the position and direction of the centesis needle in the centesis needle MPR plane by overlapping the centesis needle data with the centesis needle image data for composing with the target image data.

In the present embodiment, the centesis needle image data located at a front position the target image data and the centesis needle image data located at a backward position are discriminated by color tones. Further, it is possible to intuitively figure out the misalignment direction and size of the centesis needle to the target region by setting up a transparency of the centesis needle image data based on a crossing angle size between the target MPR plane and the centesis needle MPR plane. Consequently, it becomes possible to safely and correctly perform the examination or the medical treatment by using the centesis needle.

Figure 9:
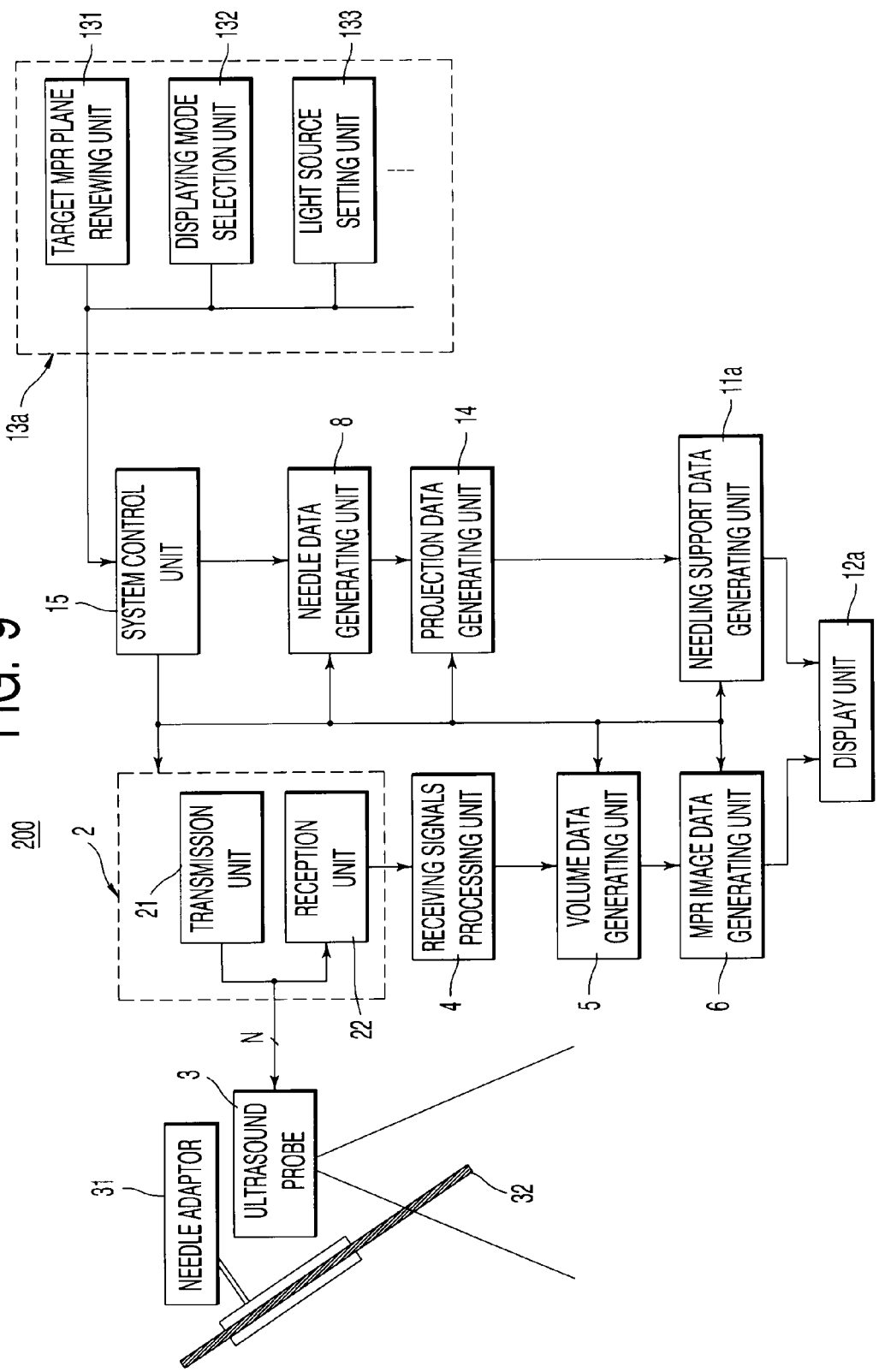
FIG. 9 is a block diagram illustrating another embodiment of the ultrasound diagnosis apparatus consistent with the present invention.

Referring with FIG. 9, another embodiment of the ultrasound diagnosis apparatus 200 consistent with the present invention is explained. To avoid a redundant explanation, corresponding units in the ultrasound diagnosis apparatus 100 shown in FIG. 1 are designated by the same reference numbers.

In this embodiment, prior to insertion of the centesis needle, the ultrasound diagnosis apparatus 200 initially sets up a target MPR plane including a target region to volume data acquired through 3D scan over 3D area including the target region. Then, the ultrasound diagnosis apparatus 200 generates target image data on the target MPR plane of the volume data acquired through 3D scan during the centesis needle insertion time. Based on the generated volume data, the ultrasound diagnosis apparatus 200 generates centesis needle data indicating positions and directions of the centesis needle. Further, the ultrasound diagnosis apparatus 200 generates centesis needle projection data by projecting the centesis needle data on the target MPR plane and also generates centesis support data by overlapping the centesis needle projection data with the target image data.

Referring with FIG. 9, the ultrasound diagnosis apparatus 200 transmits ultrasound pulses over a 3D area including a target region through an ultrasound probe 3 before and after insertion a centesis needle to a target region, and converts ultrasound reflected waves acquired through the ultrasound transmission to receiving signals. The receiving signal processing unit 4 generates B mode data by processing phase compensated and summed receiving signals. The volume data generating unit 5 generates volume data by successively storing B mode data acquired through ultrasound transmissions and receptions over the 3D area. The MPR image data generating unit 6 generates target image data by extracting the voxels of the volume data corresponded to the renewed target MPR planes by the input unit 13a.

The centesis needle data generating unit 8 generates centesis needle data indicating on positions and directions of the centesis needle by processing the volume data acquired during the centesis needle insertion time. The ultrasound diagnosis apparatus 200 consistent with this embodiment includes a projection data generating unit 14 for generating centesis needle projection data by projecting the generated centesis needle data on the target MPR plane and a centesis support data generating unit 11a for generating centesis support data by overlapping the centesis needle projection data with the target image data. The display unit 12a displays the target image data generated in the MPR image data generating unit 6 and the centesis support data generated in the centesis support data generating unit 11a.

The input unit 13a includes a target MPR plane renewing unit 131 for renewing the target MPR plane, a display mode selection unit 132 and a light source setting unit for setting up positions and directions of a light source necessary for generating the centesis needle projection data.

Figure 10:
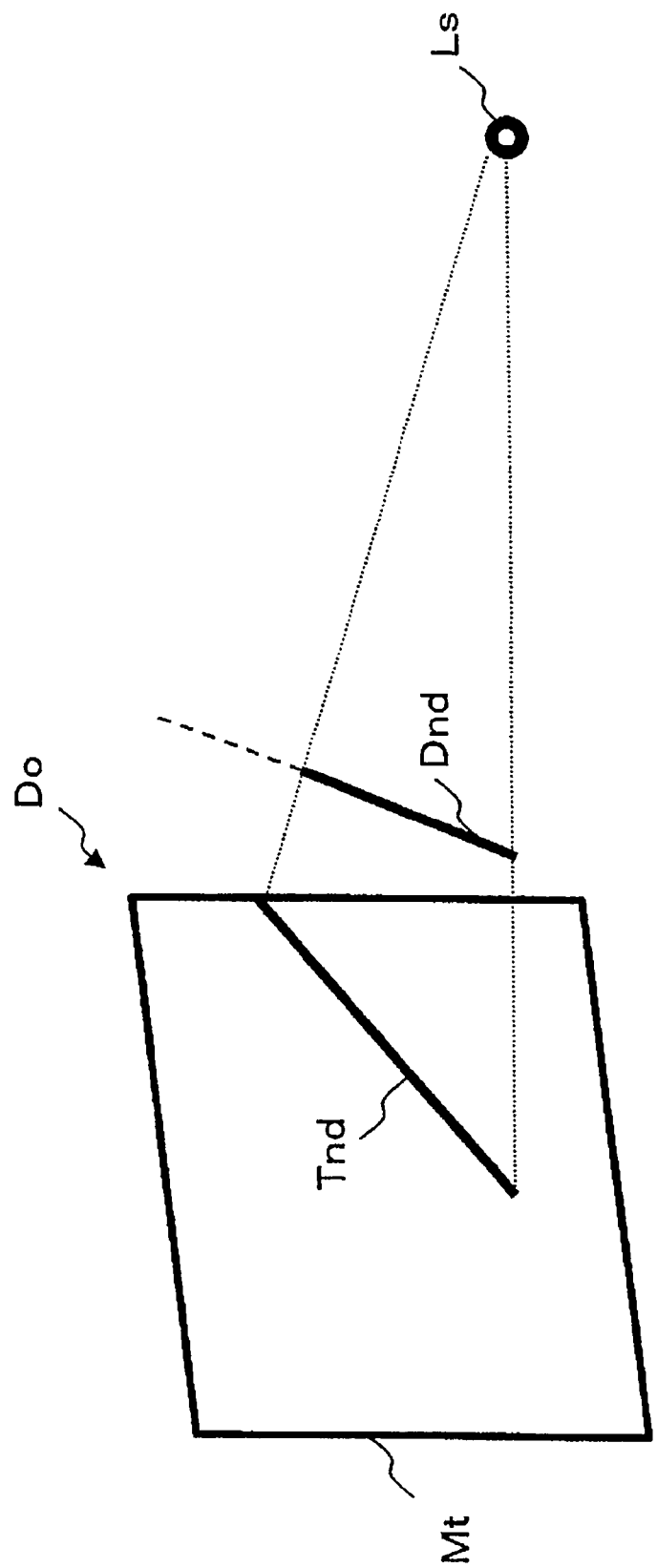
FIG. 10 schematically illustrates another method for generating the centesis needle projection data.

As illustrated in FIG. 10, a linear centesis needle data Dnd generated by the centesis needle data generating unit 6 based on the volume data during the centesis needle insertion time is projected on the target MPR plane Mt by lighting from a light source Ls under a set up condition set up by the input unit 13a. Thus, the projection data generating unit 14 generates a centesis needle projection data Do including the projection image Tnd of the centesis needle data Dnd.

The centesis support data generating unit 11a (FIG. 9) generates centesis support data by overlapping the target image data generated by the MPR image data generating unit 6 on the target MPR plane based on the volume data during the centesis needle insertion time with the centesis needle projection data generated by the projection data generating unit 14.

The display unit 12a displays the target image data generated by the MPR image data generating unit 6 based on the volume data before the centesis needle insertion time and the centesis support data generated by the centesis support data generating unit 11a during the centesis needle insertion time on a monitor.

Figure 11:
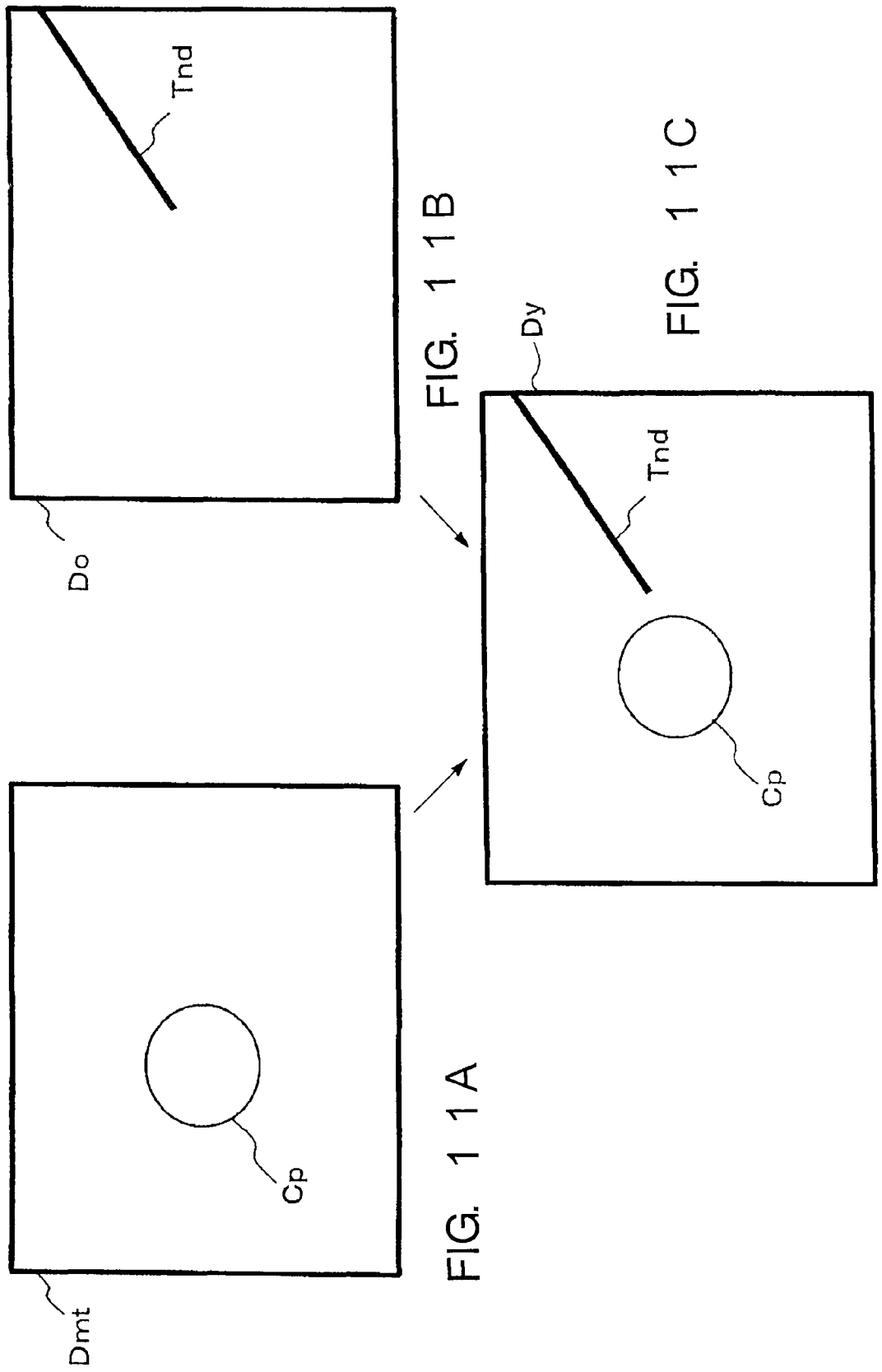
FIGS. 11A-11C are illustrations explanatory of a generation of the centesis support data.

FIGS. 11A-11C illustrate a generation of the centesis support data Dy consistent with this embodiment. FIG. 11A illustrates the target image data Dmt of the target MPR plane Mt set up on the volume data during the centesis needle insertion time. FIG. 11B illustrates the centesis needle projection data Do of the centesis needle data Dnd acquired by projecting on the target MPR plane Mt shown in FIG. 10. As illustrated in FIG. 11C, the centesis support data Dy is generated by overlapping the target image data Dmt (FIG. 11A) with the centesis needle projection data Do (FIG. 11B). In this case, the color tone or transparency for the centesis needle projection data is set up in accordance with a positional relationship between the target MPR plane Dmt and the centesis needle data Dnd.

Referring with FIG. 12, the displaying process of the centesis support data according to the present embodiment will be explained. To avoid a redundant explanation, the corresponding steps in the centesis support data displaying processes explained in FIG. 8 are assigned the same reference designations. Thus, the centesis needle data is generated based on the volume data during the centesis needle insertion time in FIG. 12, steps S1 to S8 the same as discussed above in regard to steps S1 to S8 shown in FIG. 8.

Figure 12:
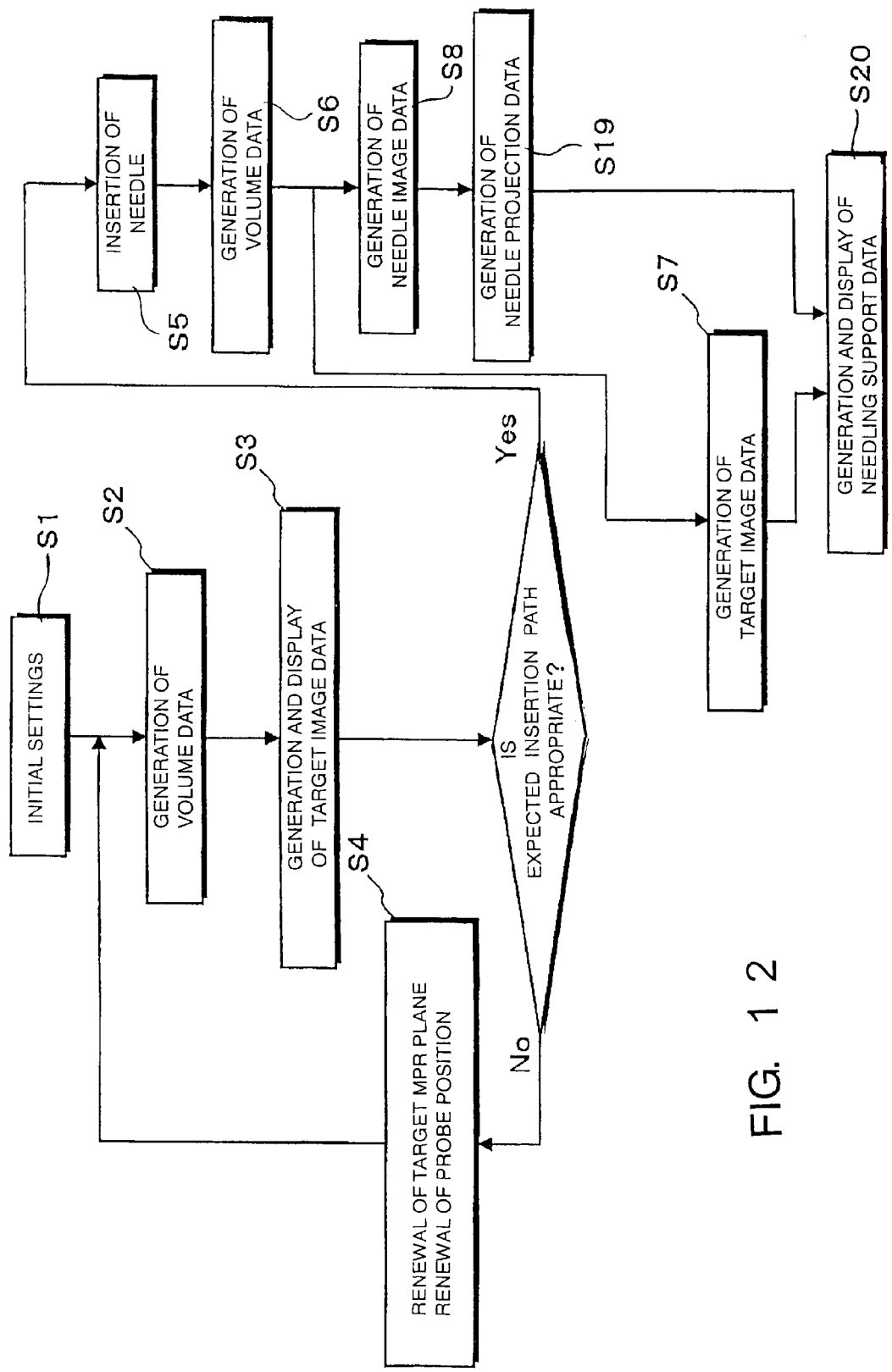
FIG. 12 is a flowchart illustrating alternative steps for displaying the centesis support data.

When the centesis needle data is generated, the projection data generating unit 14 generates centesis needle projection data by projecting the linear centesis needle data generated by the needle data generating unit 8 based on the volume data in the centesis needle insertion time on the target MPR plane by a light source set up through the input unit 13a (FIG. 12, step S19.

The centesis support data generating unit 11a generates the centesis support data by overlapping the needle projection data generated by the projection data generating unit 14 with the target image data generated by the MPR image data generating unit 6 at the target MPR plane based on the volume data during the needle insertion time. The generated centesis support data is displayed on a monitor in the display unit 12a (FIG. 12, step S20).

By repeating the steps S5 to S20 or the steps S2 to S20 shown in FIG. 12, a centesis needle is inserted into the target region under observation of the centesis support data generated and displayed in a time series.

In the above-mentioned embodiment, the centesis support data Dy is generated by overlapping the 2D needle projection data Do including the linear projection data Tnd formed by projecting the centesis needle data Dnd with the target image data Dmt. Of course, it is possible to overlap the projection image Tnd itself with the target image data Dm supposing that the projection image Tnd is the centesis needle projection data Do.

While, in the present embodiment, both the color tone and the transparency are set up to the centesis needle projection data Do, it is possible to set up either the color tone or the transparency. Further, it is possible to set up the color tone or the transparency to the target image data Dmt instead of the centesis needle projection data Do.

Similar to the previously explained embodiment, the present embodiment also can accurately and easily determine the relative position relationship of the centesis needle to the target region even when the centesis needle inserted into the patient body travels in an unexpected direction.

In particular, according to the present embodiment, when the centesis support data is generated, it can easily be discriminated when centesis needle is located at a front position of the target MPR plane when the centesis needle is located at a backward position of the target MPR plane by the color tone of the centesis needle projection data. Further, the direction or the size of the misalignment of the centesis needle to the target region can intuitively be observed by setting up the transparency of the needle projection data based on a crossing angle size formed between the target MPR plane and the centesis needle. Consequently, examination and medical treatment can effectively be performed using the centesis needle.

The present invention is not limited to the above-mentioned embodiments. It is possible to modify these embodiments. For instance, while the centesis support data is generated by composing the target image data overlapped with an insertion marker for indicating an expected insertion pathway and the centesis needle image data, the insertion marker does not necessary in the target image data for using generation of the centesis support data.

While the volume data is generated based on the B mode data acquired through 3D scans in the above-mentioned embodiment, it is possible to generate the volume data based on other ultrasound data, such as color Doppler data. Further, the volume data can be acquired through other scans, such as a convex scan, a linear scan or a radial scan.

It is therefore to be understood that within the scope of the appended claims, the present invention can be practiced otherwise than is specifically described herein.

What is claimed is:

1. An ultrasound diagnosis apparatus configured to generate centesis support data based on volume data acquired from a 3D volume including a target region during a centesis needle insertion time, the ultrasound diagnosis apparatus comprising:
   a centesis needle data generating unit configured to generate centesis needle data indicating a position and a direction of a centesis needle inserted in the 3D volume by processing the volume data;
   a centesis needle MPR cross-sectional plane setting unit configured to set up a centesis needle MPR cross-sectional plane including the centesis needle data onto the volume data;
   a crossing angle detecting unit configured to detect a crossing angle formed between a target MPR cross-sectional plane traversing the target region, which is set up on the volume data and the centesis needle MPR cross-sectional plane, the detecting determining a degree of angular difference between the target MPR cross-sectional plane and the centesis needle MPR cross-sectional plane;
   an MPR image data generating unit configured to generate a target image data on the target MPR cross-sectional plane of the volume data and a centesis needle image data on the centesis needle MPR cross-sectional plane;
   a centesis support data generating unit configured to generate the centesis support data by composing the target image data and the centesis needle image data based on the crossing angle, the centesis support data showing a relative position of the centesis needle with respect to the target MPR cross-sectional plane; and
   a display unit configured to display the centesis support data.

2. The ultrasound diagnosis apparatus according claim 1, wherein the centesis support data generating unit generates the centesis support data by composing the centesis needle image data overlapped with the centesis needle data and the target image data based on the crossing angle.

3. The ultrasound diagnosis apparatus according claim 1, wherein the display unit sets up a transparency at either one of the centesis needle image data constructing the centesis support data or the target image data based on a measure of the crossing angle.

4. The ultrasound diagnosis apparatus according claim 1, wherein the display unit sets up a color tone of the centesis needle image data constructing the centesis support data based on a positioned relationship between the centesis needle image data and the target image data.

5. The ultrasound diagnosis apparatus according claim 1, wherein the centesis needle MPR cross-sectional plane setting unit sets up a plurality of centesis needle MPR cross-sectional planes corresponding to each of a plurality of target MPR cross-sectional planes including the target region set up to the volume data.

6. An ultrasound diagnosis apparatus configured to generate centesis support data based on volume data acquired from a 3D volume including a target region during a centesis needle insertion time, the ultrasound diagnosis apparatus comprising:
   an MPR image data generating unit configured to generate target image data on a target MPR cross-sectional plane traversing the target region set up to the volume data;
   a centesis needle data generating unit configured to generate centesis needle data indicating a position or a direction of a centesis needle inserted into the 3D volume by processing the volume data;
   a projection data generating unit configured to generate centesis needle projection data by projecting the centesis needle data on the target MPR cross-sectional plane;
   a centesis support data generating unit configured to generate the centesis support data by overlapping the target image data with the centesis needle projection data, the centesis support data showing a relative position of the centesis needle with respect to the target MPR cross-sectional plane; and
   a display unit configured to display the centesis support data.

7. The ultrasound diagnosis apparatus according to claim 6, wherein the display unit sets at least either one of a color tone or a transparency of the centesis needle projection data for constructing the centesis support data based on a positioned relationship between the target MPR cross-sectional plane and the centesis needle data.

8. The ultrasound diagnosis apparatus according claim 6, wherein the projection data generating unit generates a plurality of centesis needle projection data by projecting the centesis needle data onto a plurality of target MPR cross-sectional planes including the target region set to the volume data.

9. The ultrasound diagnosis apparatus according to claim 6, wherein the centesis needle data generating unit generates the centesis needle data based on a voxel of the volume data extracted by comparing a voxel value of the volume data with a prescribed threshold for voxel detection.

10. A centesis support controlling method used for an ultrasound diagnosis apparatus, the centesis support controlling method comprising:

processing volume data acquired from a 3D volume including a target region during a centesis needle insertion time;

generating centesis needle data for indicating a position or a direction of a centesis needle inserted into the 3D volume;

setting up a centesis needle MPR cross-sectional plane including the centesis needle data on the volume data;

detecting a crossing angle formed between a target MPR cross-sectional plane traversing the target region which is set on the volume data and the centesis needle MPR cross-sectional plane, the detecting determining a degree of angular difference between the target MPR cross-sectional plane and the centesis needle MPR cross-sectional plane;

generating target image data at the target MPR cross-sectional plane of the volume data and centesis needle image data at the centesis needle MPR cross-sectional plane;

generating the centesis support data by composing the target image data and the centesis needle image data based on the crossing angle, the centesis support data showing a relative position of the centesis needle with respect to the target MPR cross-sectional plane; and displaying the centesis support data.

11. A centesis support controlling method used for an ultrasound diagnosis apparatus, the centesis support controlling method comprising:

generating target image data at a target MPR cross-sectional plane including a target region set to volume data acquired from a 3D volume including the target region during a centesis needle insertion time;

generating centesis needle data for indicating a position or a direction of a centesis needle inserted into the 3D volume by processing the volume data;

generating centesis needle projection data by projecting the centesis needle data on the target MPR cross-sectional plane;

generating the centesis support data by overlapping the centesis needle projection data onto the target image data, the centesis support data showing a relative position of the centesis needle with respect to the target MPR cross-sectional plane; and displaying the centesis support data.

* * * * *